US012343138B2

(12) United States Patent
Tabkhivayghan et al.

(10) Patent No.: US 12,343,138 B2
(45) Date of Patent: Jul. 1, 2025

(54) AI POWERED MOBILITY ASSESSMENT SYSTEM

(71) Applicant: FORESIGHTCARES INC., Matthews, NC (US)

(72) Inventors: Hamed Tabkhivayghan, Charlotte, NC (US); Mona Azarbayjani, Matthews, NC (US); Mohammadreza Baharani, Charlotte, NC (US)

(73) Assignee: FORESIGHTCARES INC., Matthews, NC (US)

( * ) Notice: Subject to any disclaimer, the term of this patent is extended or adjusted under 35 U.S.C. 154(b) by 0 days.

(21) Appl. No.: 18/960,845

(22) Filed: Nov. 26, 2024

(65) Prior Publication Data

US 2025/0176859 A1   Jun. 5, 2025

Related U.S. Application Data

(60) Provisional application No. 63/604,438, filed on Nov. 30, 2023.

(51) Int. Cl.
| A61B 5/00 | (2006.01) |
| A61B 5/11 | (2006.01) |
| A63B 24/00 | (2006.01) |
| A63B 71/06 | (2006.01) |
| A61B 90/00 | (2016.01) |

(52) U.S. Cl.
CPC .......... *A61B 5/1128* (2013.01); *A61B 5/0077* (2013.01); *A61B 5/1117* (2013.01); *A61B 5/1121* (2013.01); *A61B 5/7275* (2013.01); *A63B 24/0075* (2013.01); *A63B 71/0622* (2013.01); *A61B 5/7267* (2013.01); *A61B 2090/367* (2016.02); *A61B 2560/0223* (2013.01); *A61B 2576/00* (2013.01)

(58) Field of Classification Search
CPC ... A61B 5/1128; A61B 5/0077; A61B 5/1117; A61B 5/1121; A61B 5/7275
See application file for complete search history.

(56) References Cited

U.S. PATENT DOCUMENTS

| 11,232,694 | B2 | 1/2022 | Netscher et al. | |
| 11,900,782 | B2 | 2/2024 | Netscher et al. | |
| 2010/0002934 | A1* | 1/2010 | Sullivan | H04N 13/204 348/169 |
| 2016/0015272 | A1 | 1/2016 | Gaddipati | |
| 2016/0081594 | A1* | 3/2016 | Gaddipati | A61B 5/4824 600/595 |
| 2021/0275107 | A1* | 9/2021 | Pitters | G16H 50/50 |
| 2021/0290109 | A1 | 9/2021 | Gaddipati et al. | |
| 2024/0135796 | A1 | 4/2024 | Netscher et al. | |

* cited by examiner

*Primary Examiner* — Joel F Brutus
(74) *Attorney, Agent, or Firm* — MARSHALL, GERSTEIN & BORUN LLP

(57) ABSTRACT

To assess the mobility of a user, a mobility assessment system obtains a video of a user having a plurality of video frames from a camera. The mobility assessment system generates a three-dimensional (3D) skeleton model of the user based on the plurality of video frames, and determines a range of motion of the user based on a change in position of the 3D skeleton model over the plurality of video frames. Then the mobility assessment system provides an indication of the range of motion of the user for display. Also, the mobility assessment system delivers tailored exercises and suggestions to enhance user mobility and reduce the risk of falls.

19 Claims, 13 Drawing Sheets

AI POWERED MOBILITY ASSESSMENT SYSTEM

CROSS-REFERENCE TO RELATED APPLICATIONS

This application claims priority to U.S. Provisional Patent Application No. 63/604,438, filed Nov. 30, 2023, entitled "AI Powered Mobility Assessment System," the entire disclosure of which is hereby expressly incorporated by reference herein.

FIELD OF THE DISCLOSURE

The present disclosure relates to a mobility assessment system for determining the range of motion of a user and providing automated exercise coaching to improve the user's range of motion.

BACKGROUND

Today, there are several fitness applications which track exercise data for users. These applications can provide workout routines and/or collect reported exercise data such as the number of steps taken, stairs climbed, distance ran, amount of weight lifted, the number of repetitions at that weight, etc.

However, fitness applications currently are unable to assess whether the user performed a workout routine correctly. The fitness applications also do not provide real-time feedback to correct the user and improve their performance.

SUMMARY

The present techniques involve a method and computing device for assessing the mobility of a user by leveraging advanced computational methods to analyze video data. These techniques obtain a video of a user from a camera, which includes several video frames. Through sophisticated processing, a three-dimensional (3D) skeleton model of the user is generated based on these video frames. This model is instrumental in determining the user's range of motion by analyzing changes in the position of the 3D skeleton model across the video frames. An indication of this range of motion is then provided for display, offering valuable insights into the user's physical capabilities and potential areas for improvement.

A notable aspect of these techniques is the creation of the 3D skeleton model, which comprises multiple 3D vectors representing various body parts of the user. This detailed representation allows for a precise analysis of the user's movements. Specifically, the method includes determining the range of motion for specific joints by calculating the angle between two body parts connected by a joint. This granular approach enables a comprehensive assessment of the user's mobility across multiple joints, enhancing the accuracy of the mobility evaluation.

Furthermore, the present techniques include a calibration process to ensure the user is correctly positioned within the camera's view, enhancing the accuracy of the 3D skeleton model generation. Additionally, a field of view (FOV) calibration model is applied to adjust the 3D skeleton model according to the camera angle relative to the user. This adjustment is crucial for accurately reflecting the user's movements, considering the potential variance in camera setup across different users.

The present techniques also encompass a fall risk assessment based on the user's range of motion, providing a valuable tool for identifying users at higher risk of falling. This assessment can inform targeted interventions to enhance user mobility and reduce fall risk. Moreover, the techniques include selecting and presenting tailored exercises to the user, further supporting mobility improvement and fall risk reduction.

These techniques offer several improvements to computer processing. The generation and analysis of the 3D skeleton model require sophisticated processing capabilities, demonstrating an improvement in processing efficiency. The method efficiently handles complex computations involved in generating the 3D skeleton model and analyzing the user's range of motion, optimizing processing resources. As a result, the present techniques provide a comprehensive and efficient method for assessing user mobility through advanced video analysis and computational methods.

In an embodiment, a method for assessing mobility of a user includes obtaining, from a camera, a video of a user having a plurality of video frames, and generating a three-dimensional (3D) skeleton model of the user based on the plurality of video frames. The method also includes determining a range of motion of the user based on a change in position of the 3D skeleton model over the plurality of video frames, and providing an indication of the range of motion of the user for display.

In another embodiment, a computing device for assessing mobility of a user includes a user interface, one or more processors, and a non-transitory computer-readable memory storing instructions thereon. When executed by one or more processors, the instructions cause the computing device to obtain, from a camera, a video of a user having a plurality of video frames, and generate a three-dimensional (3D) skeleton model of the user based on the plurality of video frames. The instructions further cause the computing device to determine a range of motion of the user based on a change in position of the 3D skeleton model over the plurality of video frames, and provide, via the user interface, an indication of the range of motion of the user for display.

In yet another embodiment, a method for providing real-time exercise coaching using artificial intelligence includes determining an exercise for a user to perform, automatically providing instructions to the user for performing the exercise, obtaining, from a camera, a video of the user performing the exercise having a plurality of video frames, and generating a three-dimensional (3D) skeleton model of the user based on the plurality of video frames. The method further includes determining a movement by the user based on a change in position of the 3D skeleton model over the plurality of video frames, and automatically providing real-time feedback to the user based on the movement by the user relative to an expected motion for the exercise.

In another embodiment, a computing device for providing real-time exercise coaching using artificial intelligence includes a user interface, one or more processors, and a non-transitory computer-readable memory storing instructions thereon. When executed by one or more processors, the instructions cause the computing device to determine an exercise for a user to perform, automatically provide, via the user interface, instructions to the user for performing the exercise, obtain, from a camera, a video of the user performing the exercise having a plurality of video frames, and generate a three-dimensional (3D) skeleton model of the user based on the plurality of video frames. The instructions further cause the computing device to determine a movement by the user based on a change in position of the 3D skeleton model over the plurality of video frames, and automatically provide, via the user interface, real-time feedback to the user based on the movement by the user relative to an expected motion for the exercise.

BRIEF DESCRIPTION OF THE DRAWINGS

The following detailed description will be more easily and better understood when considered in conjunction with the following figures, in which like reference numbers are employed to designate like structures. It should be understood that, with the exception of magnified images, the drawings are not to scale, as scaled drawings would not facilitate an understanding of the depicted structures.

DETAILED DESCRIPTION

Although the following text sets forth a detailed description of senior health monitoring and fall risk assessment, it should be understood that the scope of AI-based software and systems architecture for physical mobility assessment also applies to other parties, such as athletes. For various domains such as hospitals and older adult communities, gyms, and training facilities, several exercises and different AI-based assessment analyses can be provided by using current technology which could still fall within the scope of the claims.

Figure 1:
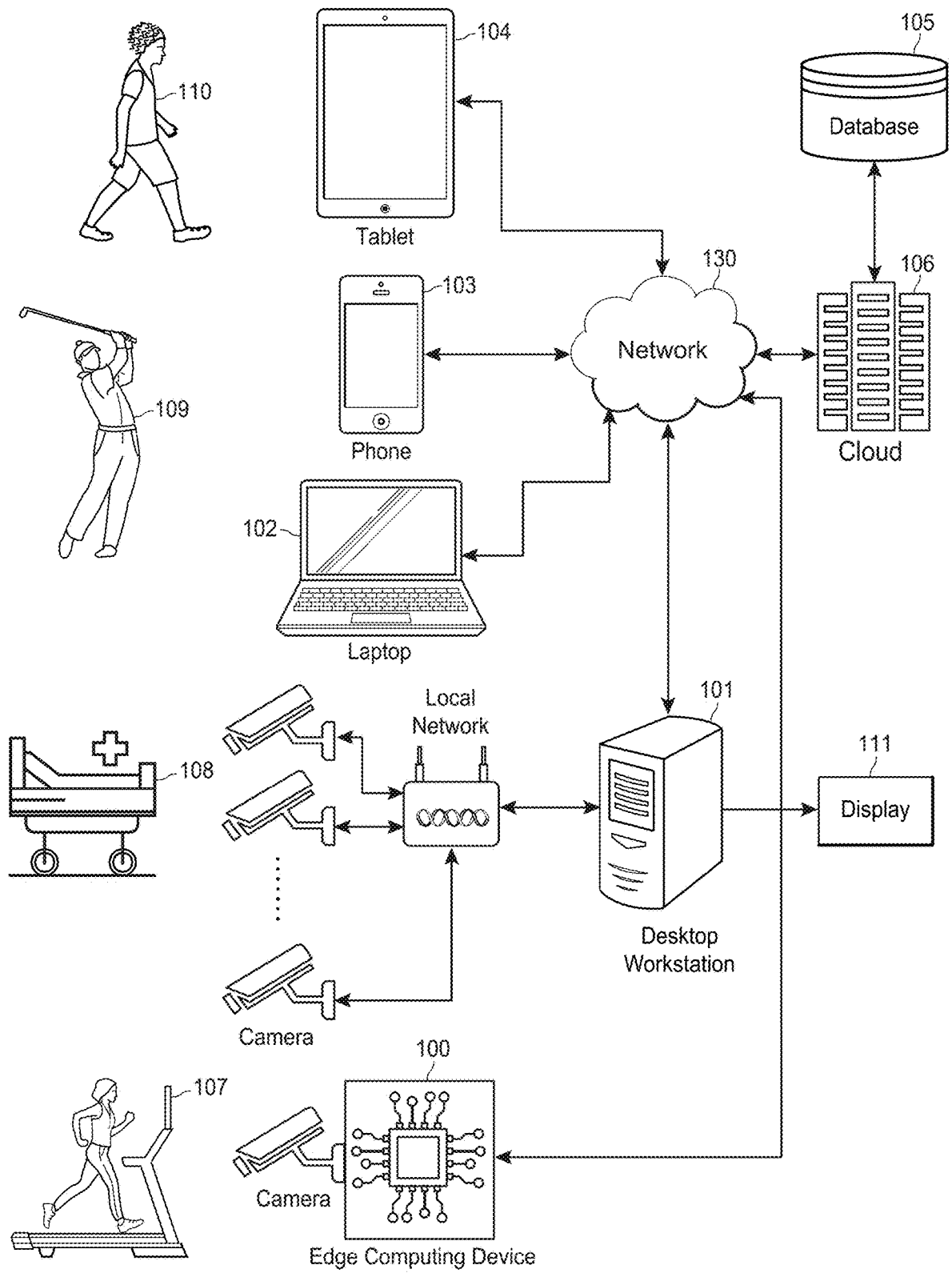
FIG. 1 is a block diagram of an example communication system in which techniques can be provided for health monitoring and assessment.

FIG. 1 illustrates an example communication system 1 for performing health monitoring and mobility assessment. The communication system 1 includes several client computing devices 101-104, such as a desktop computer 101, a laptop computer 102, a smartphone 103, a tablet computer 104, a personal digital assistant (PDA), a wearable device such as a smart watch or smart glasses, a virtual reality headset, etc. The client computing devices 101-104 may be operated by users who are exercising and having their mobility assessed. These users may be exercising in gyms 107, in hospitals and/or senior communities 108, at training facilities 109, at home 110, or in any suitable location.

In some implementations, the client computing devices 101-104 may communicate over a network 130 with client computing devices 101-104 operated by a physical therapist, fitness trainer, or coach to monitor the performance of the users.

Each client computing device 101-104 may include one or more processor(s) and a memory storing machine-readable instructions executable on the processor(s). The processor(s) may include one or more general-purpose processors (e.g., CPUs), and/or special-purpose processing units (e.g., graphical processing units (GPUs)). The memory can be, optionally, a non-transitory memory and can include one or several suitable memory modules, such as random access memory (RAM), read-only memory (ROM), flash memory, other types of persistent memory, etc.

The client computing device 101-104 may further include a global positioning system (GPS) or another suitable positioning module, a network module, a user interface 111 for displaying exercise videos, mobility assessments, and real-time feedback, and an input/output (I/O) module. The network module may include one or more communication interfaces such as hardware, software, and/or firmware of an interface for enabling communications via a cellular network, a Wi-Fi network, or any other suitable network such as a network 130, discussed below. The I/O module may include I/O devices capable of receiving inputs from, and providing outputs to, the ambient environment and/or a user. The I/O module may include a touch screen, display, keyboard, mouse, buttons, keys, microphone, speaker, etc.

In some implementations, each client computing device 101-104 include a camera for capturing a video of the user as the user performs an exercise. In other implementations, a client computing device 101-104 is communicatively coupled to a camera via a network 130. For example, cameras may be located in a gym 107, hospital, or senior community 108 which capture video of a user as the user exercises. The cameras may transmit the video to a client computing device 101-104 of a user to assess the user's mobility.

The memory of the client computing device 101-104 may store an operating system (OS), which can be any type of suitable mobile or general-purpose operating system. The memory may also include a mobility assessment application that can instruct the user to perform exercises and assess the mobility of the user based on the user's performance of the exercises.

The client computing device 101-104 may communicate with a server device 106, such as a cloud computing system and/or an edge computing device 100 (e.g., NVIDIA® Jetson Xavier™) via a network 130. The network 130 may include one or more of an Ethernet-based network, a private network, a cellular network, a local area network (LAN), and/or a wide area network (WAN), such as the Internet.

In certain aspects, the network 130 may include any communication link suitable for short-range communications and may conform to a communication protocol such as, for example, Bluetooth™ (e.g., BLE), Wi-Fi (e.g., Wi-Fi Direct), NFC, ultrasonic signals, etc. Additionally, or alternatively, the network 130 may be, for example, Wi-Fi, a cellular communication link (e.g., conforming to 3G, 4G, or 5G standards), etc. In some scenarios, the network 130 may also include a wired connection.

The server device 106 may be a remotely located server, such as a cloud computing device which can perform some or all of the actions described herein with respect to the client computing device 101-104. The server device 106 may be part of a cloud service such as Amazon Web Services (AWS) or Azure. The server device 106 can be used for data gathering and distribution among nodes if necessary. For example, the server device 106 may collect training data from several client computing devices 101-104 to train a field of view (FOV) calibration model to adjust a 3D skeleton model to account for different camera angles when capturing video of a user. The server device 106 may then provide the FOV calibration model to a client computing device 101-104 for the client computing device 101-104 to adjust a 3D skeleton model for the user based on the camera angle of the camera capturing video of the user.

The server device 106 and/or the edge computing device 100 may also receive video of the user from a camera. The server device 106 and/or the edge computing device 100 may then transmit the video to the user's client computing device 101-104 to perform a mobility assessment of the user via the mobility assessment application. In other implementations, the server device 106 and/or the edge computing device 100 may perform the mobility assessment and provide an indication of the mobility assessment to the user's client computing device 101-104.

Additionally, the server device 106 and/or the edge computing device 100 may store the mobility assessment in a database 105. In this manner, when the user requests another mobility assessment, the mobility assessment application may compare the current mobility assessment to previous mobility assessments to track the progress of the user. Additionally, the mobility assessment application may analyze the previous mobility assessments to identify body parts that the user needs to work on and corresponding exercises to focus on those body parts. In this manner, the mobility assessment application adapts to the user's performance to concentrate exercises on parts of the body where the user needs to improve their mobility the most. The database 105 may also store user identification information, physical therapist (PT) information, etc.

Figure 2:
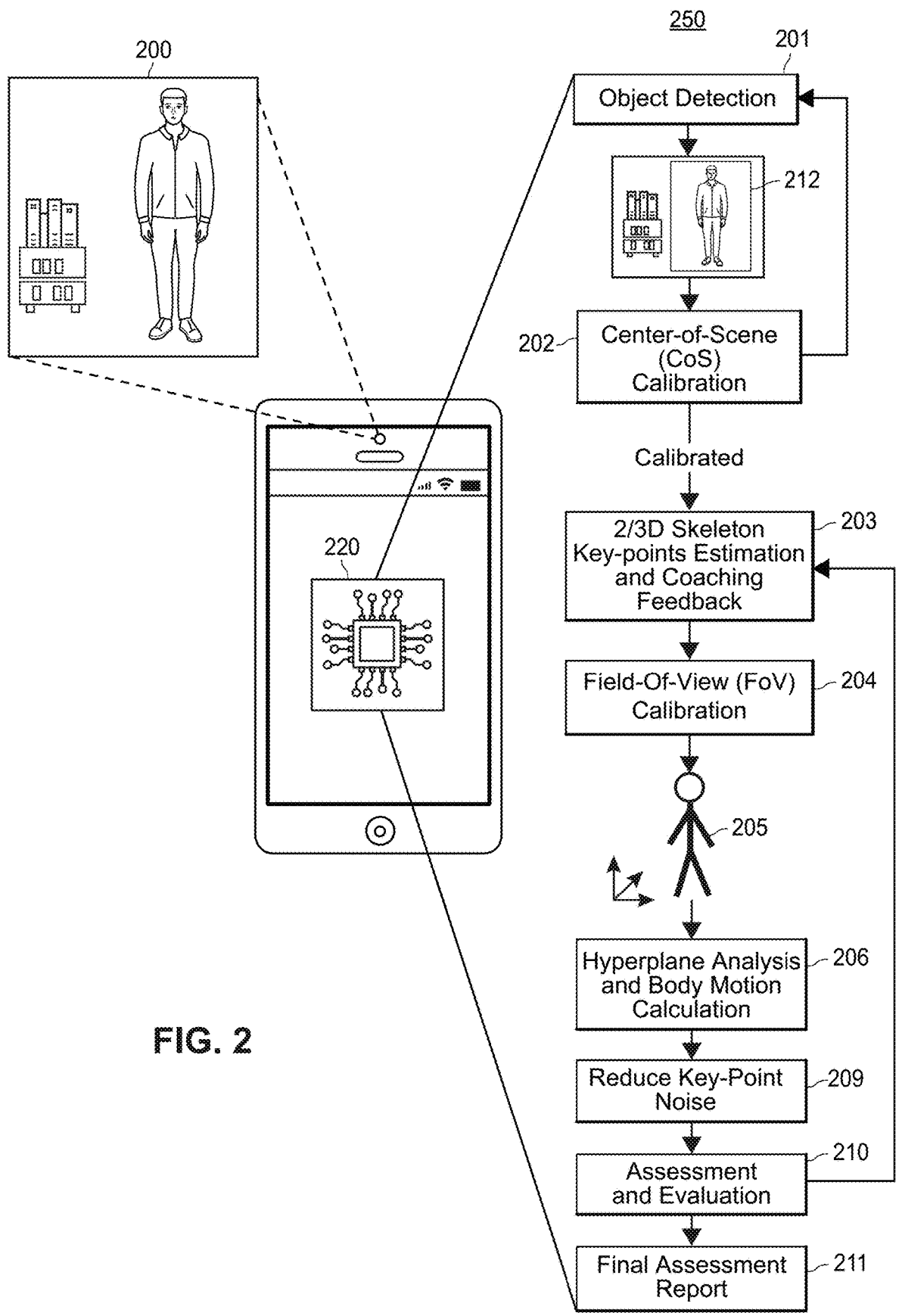
FIG. 2 illustrates a flow diagram of an example method for performing a mobility assessment for a user, which can be implemented in a client device.

FIG. 2 illustrates a flow diagram of an example method 250 for performing a mobility assessment for a user, which can be implemented in a client computing device 101-104. In some implementations, the method 250 is implemented by the mobility assessment application.

The mobility assessment application may include the following software components, a human detector, a 3D skeleton pose estimator, and an FOV calibration model. The user may position the camera of the client computing device 101-104 to face themselves so that the client computing device 101-104 can perform the mobility assessment. At block 201, the mobility assessment application obtains an image or video 200 of the user from a camera and begins buffering the video frames. The image 200 may be a two-dimensional (2D) image(s) or video frame(s), which are each a group of pixels in width and height typically captured from a digital camera. The mobility assessment application analyzes the buffered video frames 200 to perform object detection and identify a person 212 within the video frames 200. For example, the image 200 includes a person 212 and another object. The mobility assessment application identifies the person 212 within the image by identifying features of each object within the image 200, such as the geometry of the edges of the object, and RGB pixel values or colors within the object.

The features of the object may also include facial features such as the geometry and RGB pixel values or colors for eyes, a mouth, and a nose. These features may be identified by detecting stable regions within the object that are detectable regardless of blur, motion, distortion, orientation, illumination, scaling, and/or other changes in camera perspective. The stable regions may be extracted from the object using a scale-invariant feature transform (SIFT), speeded up robust features (SURF), fast retina keypoint (FREAK), binary robust invariant scalable keypoints (BRISK), or any other suitable computer vision techniques. In some embodiments, keypoints may be located at high-contrast regions of the object, such as edges within the object. A bounding box may be formed around a keypoint and the portion of the object created by the bounding box may be a feature.

The mobility assessment application may compare the features identified for the object to features from template objects (also referred to herein as "template features") using image classification and/or machine learning techniques, where at least some of the template objects represent a person. The machine learning techniques may include linear regression, polynomial regression, logistic regression, random forests, boosting, nearest neighbors, Bayesian networks, neural networks, support vector machines, or any other suitable machine learning technique. For example, the widths and heights of people may be stored as template features along with skin tones for people, the widths and heights of noses, mouths, eyes, and their respective positions relative to each other. The template objects may also include other representations which are not of humans, such as representations of computers, animals, furniture, plants, etc. Then each of these template features may be compared to the features for an object.

In some embodiments, the template features may be compared to the features for an object using a nearest neighbors algorithm. The nearest neighbors algorithm may identify template features which are the closest to the features of the object by creating numerical representations of the features to generate feature vectors, such as a pixel width and height of a nose, RGB pixel values for the nose, and pixel distances from the edges of the face to the top, bottom, and sides of the nose, for example. The numerical representations of the features or feature vectors of the object may be compared to the feature vectors of template objects to determine a vector distance between the features of the object and each template object. The mobility assessment application may then determine whether the object is a human based on the amount of similarity, or the vector distance in the nearest neighbors algorithm, between the features for the object and the features for template objects that represent a human. If the closest template objects represent a human, the object is identified as a human.

Once a person is detected, the focus shifts to identifying specific body parts. This is achieved through pose estimation algorithms, which can be either 2D or 3D. These algorithms analyze the pixels in the image to find patterns that match the trained model's understanding of human anatomy, such as the position of joints and limbs.

Figure 5A:
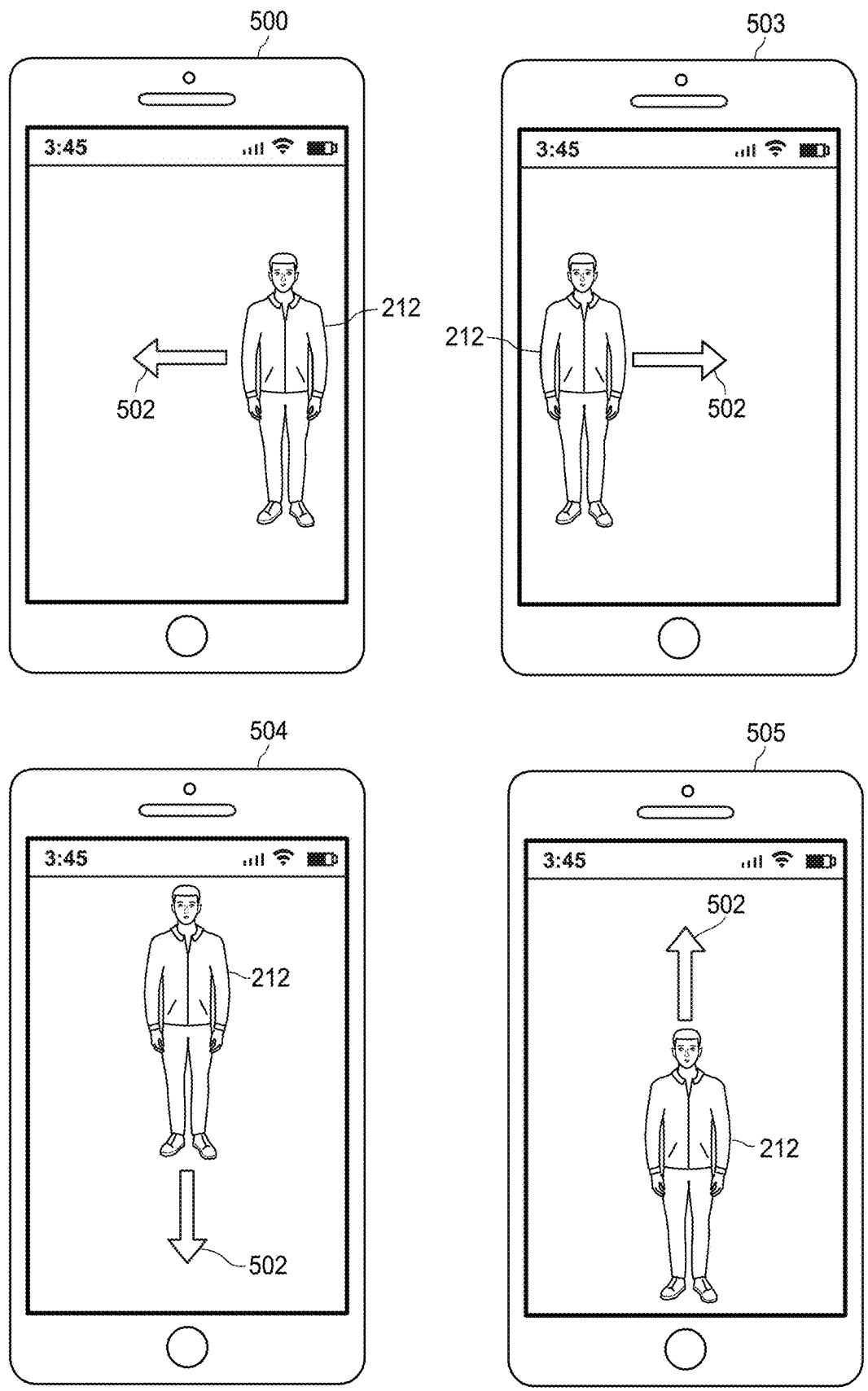
FIG. 5A illustrates example calibration displays which may be presented on the user interface of a client device for performing a Center-of-Scene (CoS) calibration to ensure that the user is positioned in the center of the camera view.

Then at block 202, the mobility assessment application performs a Center-of-Scene (CoS) calibration 202 guides the user to the appropriate location based on the target exercise. An example of the CoS calibration 202 is shown in FIG. 5A. FIG. 5A illustrates example calibration displays 500 and 503-505 which may be presented on the user interface 111 of the client computing device 101-104 to guide the user to the center of the camera view. When the user positions the camera of the client computing device 101-104 to capture video frames of the user, the mobility assessment application may overlay the video frames 200 of the user with indications 502 such as arrows directing the user to position themselves in the center of the camera view. In some implementations, the mobility assessment application may present audio instructions via the speakers.

As the user moves the camera view, the mobility assessment application may change the direction of the arrows 502, for example if the user moves too far in one direction. Additionally, the mobility assessment application calculates an intersection-of-Union (IoU) between the camera frame size and the person bounding box to ensure the body area covers the camera frame efficiently and it is within the predefined thresholds.

Figure 5B:
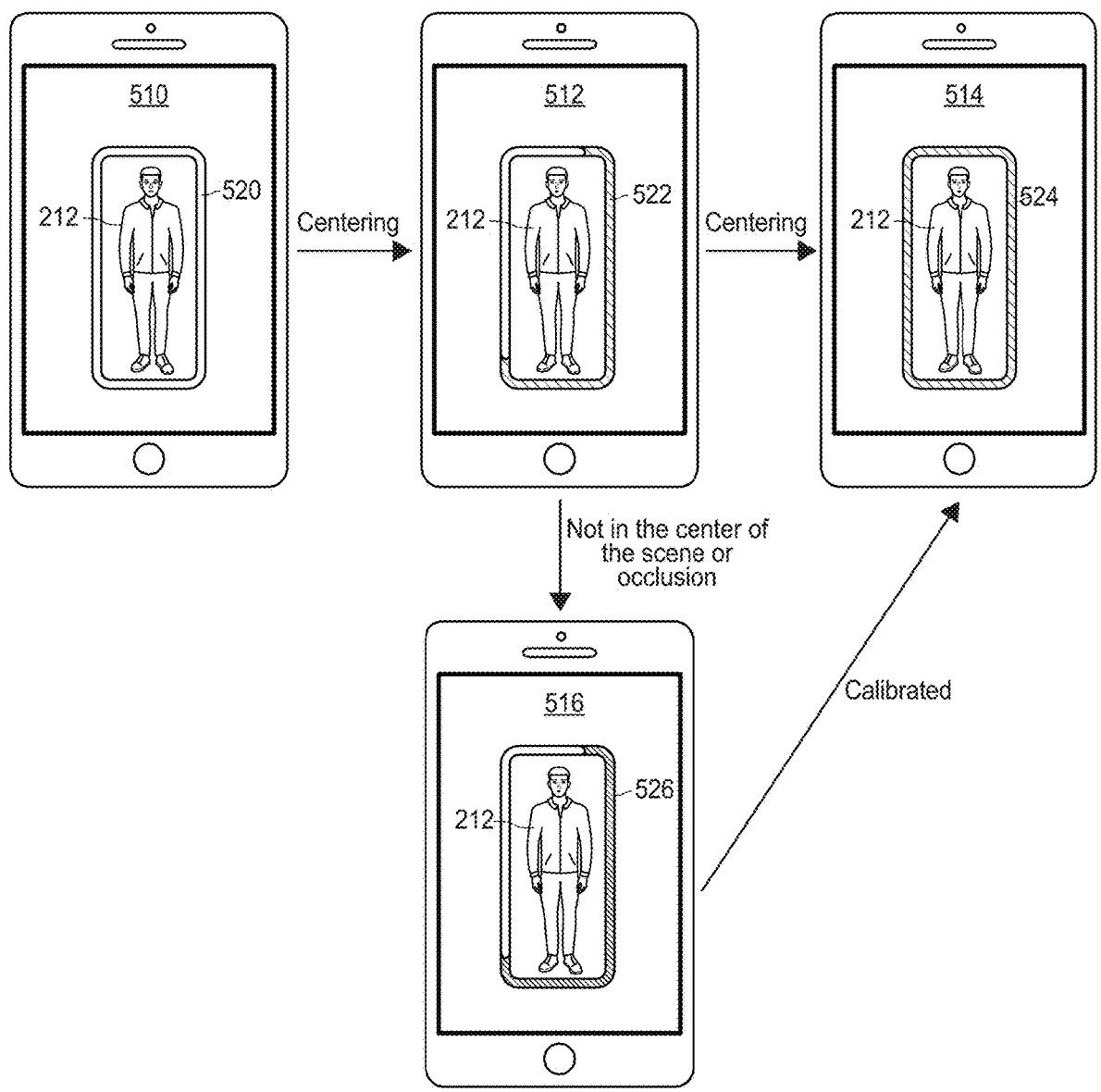
FIG. 5B illustrates additional calibration displays which may be presented on the user interface of a client device for performing a CoS calibration to ensure that the user is positioned in the center of the camera view.

Another example of the CoS calibration 202 is shown in FIG. 5B, which may be referred to as an advanced CoS calibration. FIG. 5B illustrates example calibration displays 510-516 which may be presented on the user interface 111 of the client computing device 101-104 to guide the user to the center of the camera view. When the user positions the camera of the client computing device 101-104 to capture video frames of the user, the mobility assessment application may overlay the video frames 200 of the user with indications 520-526 such as a progress bar directing the user 212 or person of interest to position themselves in the center of the camera view. The progress bar 520-526 may include two colors, such as green and red where a green color 522 indicates the user 212 is correctly aligned in the center of the screen and a red color 526 indicates the user 212 is not in the center of the screen or the user is being occluded by another person or object. Additionally, the progress bar 522 begins to fill as the features of the user 212 are captured and populated with embeddings from the FOV calibration model to generate a 3D skeleton model of the user 212 with 3D vectors representing the user's body parts with line segments in 3D space. When the progress bar 524 is completely full, calibration is complete.

Figure 5C:
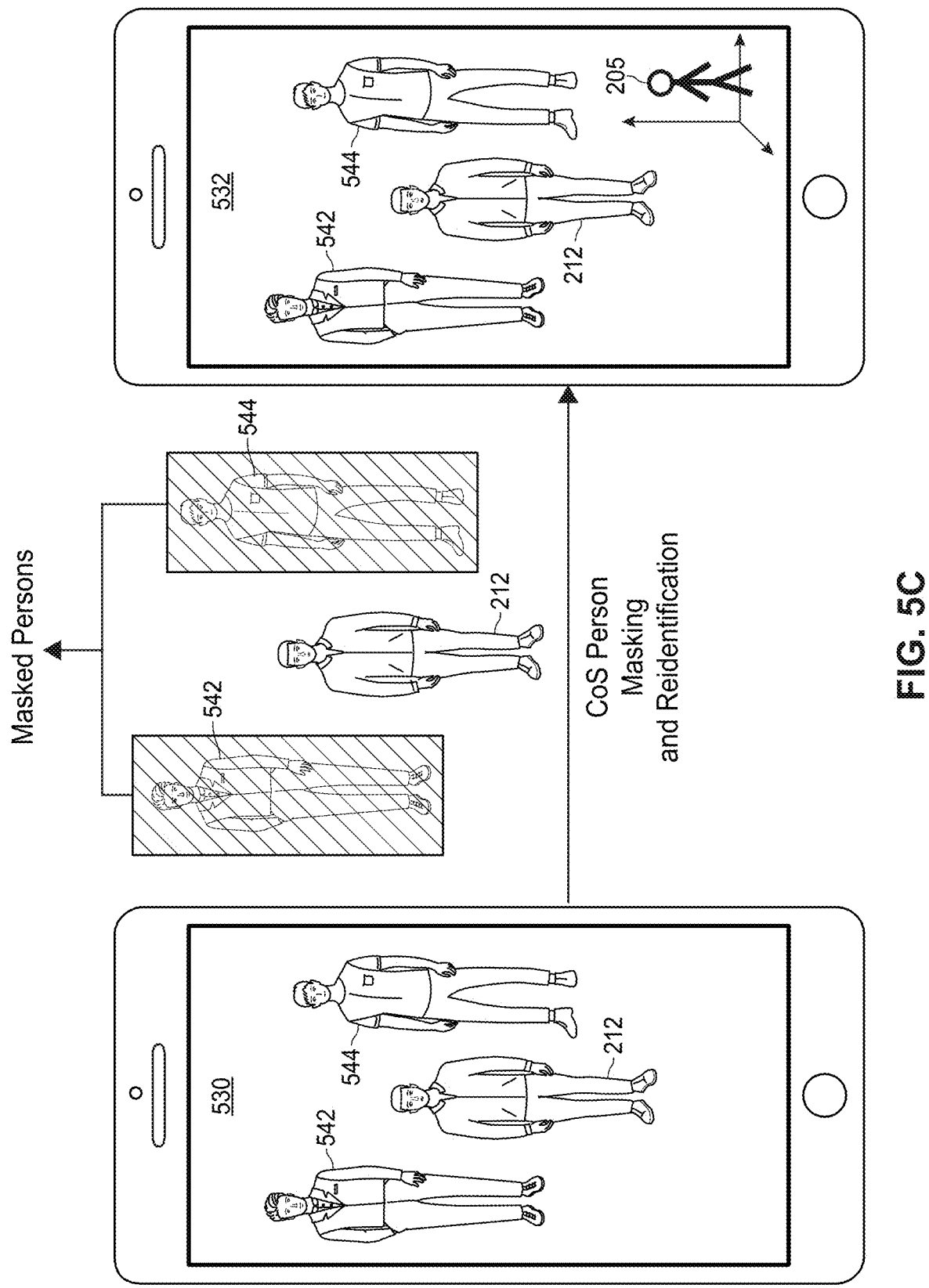
FIG. 5C illustrates example masking displays which may be presented on the user interface of a client device for masking other people in the camera view.

In some implementations, the mobility assessment application may identify additional people in the camera view. The CoS calibration 202 may filter out the other people or objects in the camera view during calibration, so that coaches, physical therapists, caregivers, and others can stand near the person of interest 212 without interference. FIG. 5C illustrates example masking displays 530, 532 which may be presented on the user interface 111 of the client computing device 101-104 for masking other people 542, 544 in the camera view.

As shown in FIG. 5C, the image or video frame 530 includes the person of interest 212 and two other people 542, 544. The mobility assessment application identifies the other people 542, 544 by identifying features of each object within the image or video frame 530 and determining there are three people 212, 542, 544 in the image or video frame 530. Then the mobility assessment application may compare the features of the person of interest 212 to the features of each of the people 212, 542, 544 identified in the image or video frame 530 to determine which person in the image or video frame 530 is the person of interest.

Upon determining that the person 212 is the person of interest, the mobility assessment application may mask or filter out the other people 542, 544. More specifically, the mobility assessment application may capture movement by the person of interest 212 by detecting changes in the positions of the person of interest's body parts without capture movement of the other people 542, 544.

Figure 5D:
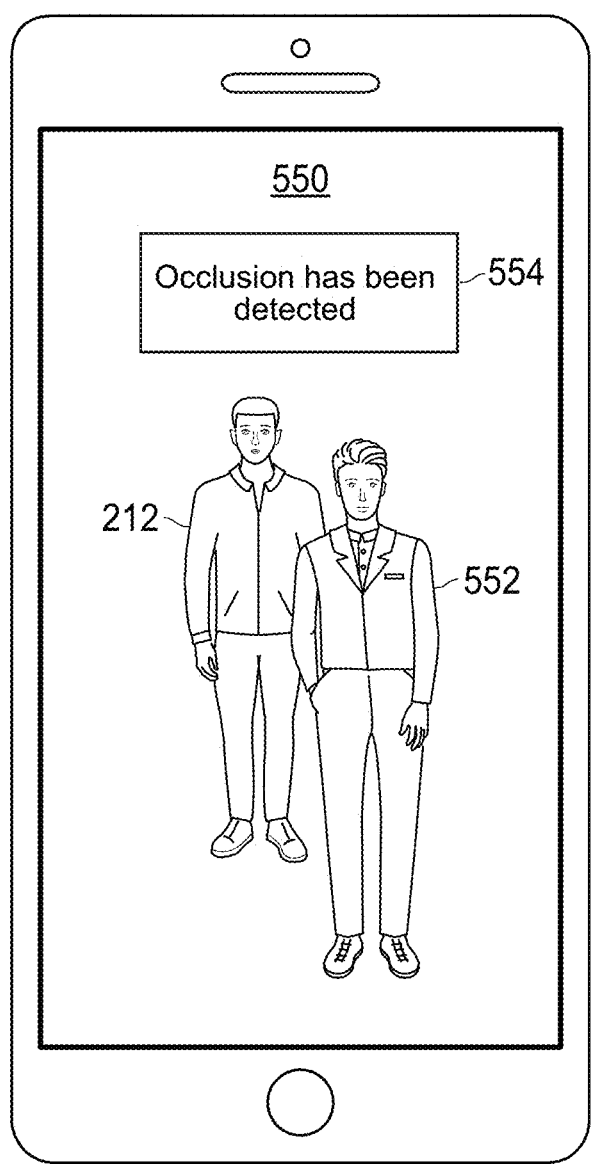
FIG. 5D illustrates an example alert display which may be presented on the user interface of a client device to alert the user when they are being occluded by another person or object.

Also in some implementations, the mobility assessment application may determine when the person of interest 212 is being occluded by another person or object. The mobility assessment application may provide a visual or audio alert if a person or object is obstructing the person of interest to prevent the person of interest from being obstructed so that the range of motion of the person of interest is detected accurately. FIG. 5D illustrates an example alert display 550 which may be presented on the user interface 111 of the client computing device 101-104 to alert the user 212 when they are being occluded by another person or object. As shown in FIG. 5D, the image or video frame 550 includes another person 552 obstructing the person of interest 212.

The mobility assessment application identifies the other person 552 by identifying features of each object within the image or video frame 550 and determining there are two people 552 in the image or video frame 550. Then the mobility assessment application may compare the features of the person of interest 212 to the features of each of the people 212, 552 identified in the image or video frame 550 to determine which person in the image or video frame 550 is the person of interest. The mobility assessment application may determine that the other person 552 is occluding the person of interest 212 if the person of interest 212 and the other person 552 are within a threshold distance of each other, for example. In another example, the mobility assessment application may be unable to detect a portion of the person of interest's 212 body and the other person 552 may be detected at the location where the portion of the person of interest's 212 body should be. Still further, the mobility assessment application may generate bounding boxes around the person of interest 212 and the other person 552, and may determine that the other person 552 is occluding the person of interest 212 when the bounding boxes overlap. In any event, the mobility assessment application may determine that the other person 552 is occluding the person of interest 212 based on any combination of these factors or in any other suitable manner.

Turning back to FIG. 2, once the camera view is calibrated such that the user is in the center, the mobility assessment application generates a 3D skeleton model 205 of the user based on the location of the detected person within the video frames 200 (block 203). The 3D skeleton model 205 includes 3D vectors representing the user's body parts with line segments in 3D space. For example, the 3D skeleton model 205 may include a line segment for each of the user's hands, a line segment for each of the user's forearms, a line segment for each of the user's humeri, a line segment for the user's neck, a line segment for the user's clavicle, a line segment for the user's right side, a line segment for the user's left side, a line segment for the user's hips, a line segment for each of the user's femurs, a line segment for each of the user's tibias, a line segment for each of the user's feet, etc.

Generating the 3D skeleton model 205 may include mapping the 2D coordinates (x, y) obtained from the image 200 to 3D coordinates (x, y, z) by combining multiple images of the user 212 captured from different angles or FOVs to generate a 3D reconstruction. This step creates a digital skeleton that mirrors the user's posture and movements. To detect the movement of the person's body parts, the mobility assessment application continuously analyzes sequential frames of the video, tracking the change in position of each joint or limb over time. This movement data is then applied to the 3D skeleton model 205, allowing it to mimic the user's actions in real-time.

In some implementations, the mobility assessment application performs an FOV calibration to adjust the 3D skeleton model 205 in accordance with a camera angle of the camera relative to the user. More specifically, the mobility assessment application may obtain a trained FOV calibration model from the server device 106. Since every user may set up the camera at a different angle, the server device 106 may generate a new model and training mechanism to remove unintentional bias caused by various fields of view. In order to train the FoV calibration model, the server device 106 obtains image and/or motion data from several camera angles.

Figure 3:
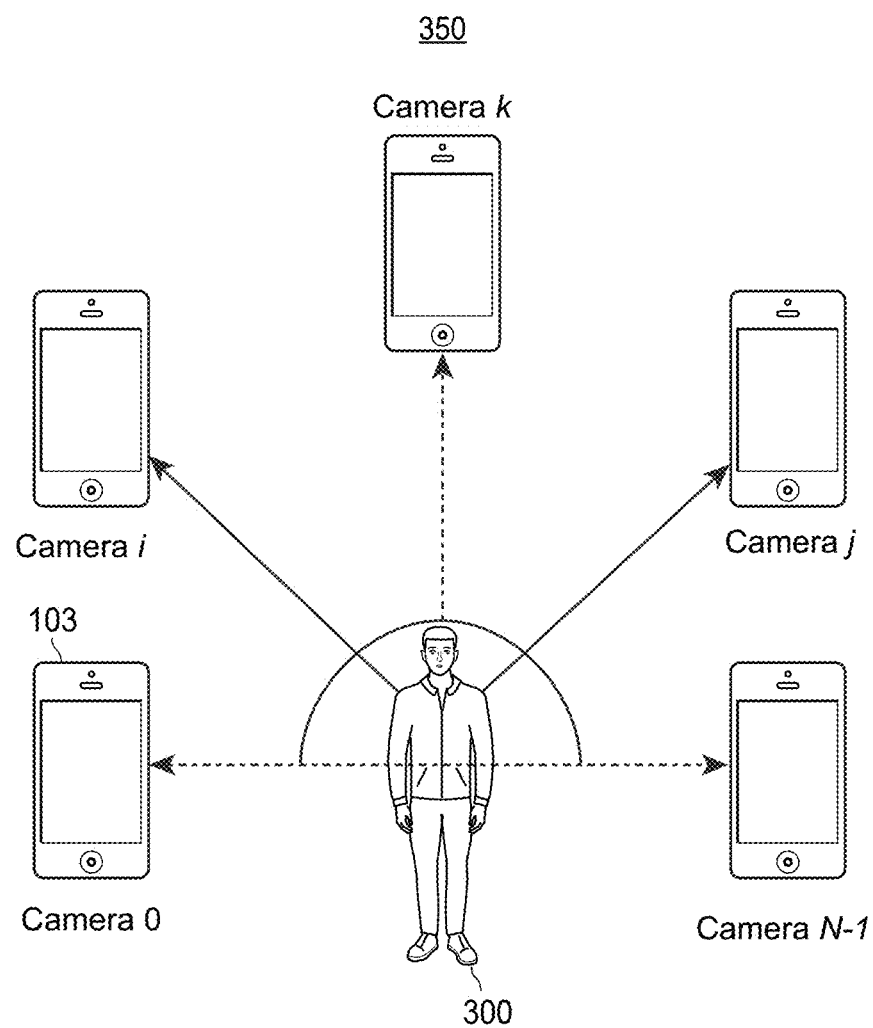
FIG. 3 illustrates an example environment for creating a dataset to train a Field-of-View (FoV) calibration model.

FIG. 3 illustrates an example environment 350 for creating a dataset to train the FOV calibration model. The example environment includes N cameras 103 and a training subject with attached motion capture sensors 300. The N cameras 103 each have a different FoV with respect to the training subject. For example, camera 0 may be to the left of the training subject, camera i may be to the left and above the training subject, camera k may be directly above the training subject, camera j may be to the right and above the training subject, and camera N− 1 may be to right of the training subject. The high-speed motion capture sensors 300 may record the person's body movement while the training subject performs different exercises.

Additionally, as the training subject performs different exercises, each camera 103 captures video frames of the training subject. The server device 106 or another computing device analyzes the video frames to generate 3D skeleton models in each video frame for each camera 103. The server device 106 may then generate the FOV calibration model using the 3D skeleton models as model input and more specifically 3D vector data from the 3D skeleton models, and the actual position of the training subject using the high-speed motion capture sensors 300 as ground truth.

The server device 106 may generate the FOV calibration model using any suitable machine learning techniques, such as linear regression, polynomial regression, logistic regression, random forests, boosting, nearest neighbors, Bayesian networks, neural networks, support vector machines, etc. For example, the server device 106 may use a loss function to generate the FOV calibration model which may be based on the Mean-Square-Error (MSE) of peer-to-peer length or the Euler angle-based error function. The server device 106 may generate the FOV calibration model to adjust 3D skeleton models spatially, i.e., on a per frame basis, and/or temporally, i.e., across a sequence of frames based on the application requirements.

Turning back to FIG. 2, the server device 106 may provide the trained FOV calibration model to the mobility assessment application. The mobility assessment application may then apply the 3D skeleton model 205 generated for the user (e.g., spatially and/or temporally) to the FOV calibration model to adjust the 3D skeleton model 205 to account for the camera angle of the camera and more accurately reflect the movement of the user (block 204).

At block 206, the mobility assessment application performs a hyperplane analysis and a body motion calculation using the 3D skeleton model 205 representing the user across several video frames as the user performs exercises. More specifically, as an initial assessment, the mobility assessment application may obtain a predetermined list of exercises to determine the user's mobility in their ankles, knees, hips, shoulders, elbows, wrists, neck, etc. The mobility assessment application may play exercise videos via the speakers and user interface 111 of the client computing device 101-104 which demonstrate the exercises that the user needs to perform. In other implementations, the mobility assessment application may automatically provide instructions to the user on how to perform the exercise in any other suitable manner. As the user attempts to mimic the exercises demonstrated in the videos, the mobility assessment application captures video frames of the user, generates the 3D skeleton model, and determines the user's range of motion based on positions and/or changes in position of the 3D vectors included in the 3D skeleton model.

The mobility assessment application may generate a separate range of motion metric for several body parts, such as joints. For example, the mobility assessment application may measure angles between different 3D vectors representing two adjacent body parts which connect at a body joint to estimate the range of motion of a particular joint. The angles per joint are smoothed across received frames to reduce noise. More specifically, to determine the range of motion of a user's right shoulder for example, the mobility assessment application may measure the angle between a 3D vector representing the user's right arm and a 3D vector representing the user's clavicle. To determine the range of motion of a user's left hip for example, the mobility assessment application may measure the angle between a 3D vector representing the user's pelvis and a 3D vector representing the user's left leg.

For the cases where an inclination needs to be calculated between two unattached body parts, such as an angle between a shoulder and the spine, a hyperplane is created perpendicular to a body part, and the mobility assessment application calculates the angle between that body part and the hyperplane.

At block 209, the mobility assessment application performs noise reduction and smoothing to the range of motion metrics by for example, applying averaging mechanisms such as weighted window averaging to smooth the final range of movement by reducing the noise of estimated angles.

Then at block 210, the mobility assessment application generates an assessment and performance evaluation of the user's range of motion. In some implementations, the mobility assessment application may aggregate or combine the range of motion metrics for each body part/joint in any suitable manner to generate an overall range of motion for the user. For example, the overall range of motion may be a metric which is an average or a weighted average of the range of motion metrics for each body part/joint. The weights may be assigned to emphasize certain body parts/joint and deemphasize others. Also in some implementations, the user, PT, or coach can select a customized function, such as weighted averaging, to emphasize more important body parts/joints.

In other implementations, the overall range of motion may be a category selected from a group of categories, such as "Very Poor," "Poor," "Average," "Good," "Very Good," and "Excellent." The mobility assessment application may determine the category to assign to the overall range of motion by comparing the overall range of motion metric to threshold metrics. For example, if the overall range of motion metric is below a first threshold metric, the mobility assessment application may determine that the overall range of motion for the user is "Very Poor." If the overall range of motion metric is above the first threshold metric but below a second threshold metric, the mobility assessment application may determine that the overall range of motion for the user is "Poor" and so on.

Additionally, the mobility assessment application may assign categories to the range of motion metrics for each body part/joint in a similar manner. For example, the mobility assessment application may determine that the user has "Poor" mobility in their knee but "Excellent" shoulder mobility.

The mobility assessment application may also perform a fall risk assessment based on the overall range of motion of the user and/or the range of motion metrics for each body part/joint. In some implementations, the mobility assessment application may generate a risk of falling metric which is inversely proportional to the overall range of motion metric for the user. In some implementations, the risk of falling metric may be based on the range of motion metrics for lower body parts/joints, such as hips, knees, and ankles. The mobility assessment application may generate a weighted average of the range of motion metrics for individual body parts/joints and may assign higher weights to the lower body parts/joints to determine the risk of falling metric. In other implementations, the risk of falling metric may be solely based on the range of motion metrics for lower body parts/joints.

The mobility assessment application may also assign a category to the risk of falling selected from a group of categories, such as "High," "Medium" or "Low." For example, the mobility assessment application may determine the risk of falling is "High" when the overall range of motion for the user is "Very Poor," and may determine that the risk of falling is "Low" when the overall range of motion for the user is "Very Good."

In any event, at block 211, the mobility assessment application generates a final assessment report for the user based on the overall range of motion for the user, the range of motion metrics for individual body parts/joints, and/or the risk of falling for the user. Then the mobility assessment application may present a final assessment display on the user interface 111 of the client computing device 101-104. An example final assessment display 700 is illustrated in FIG. 7.

Figure 7:
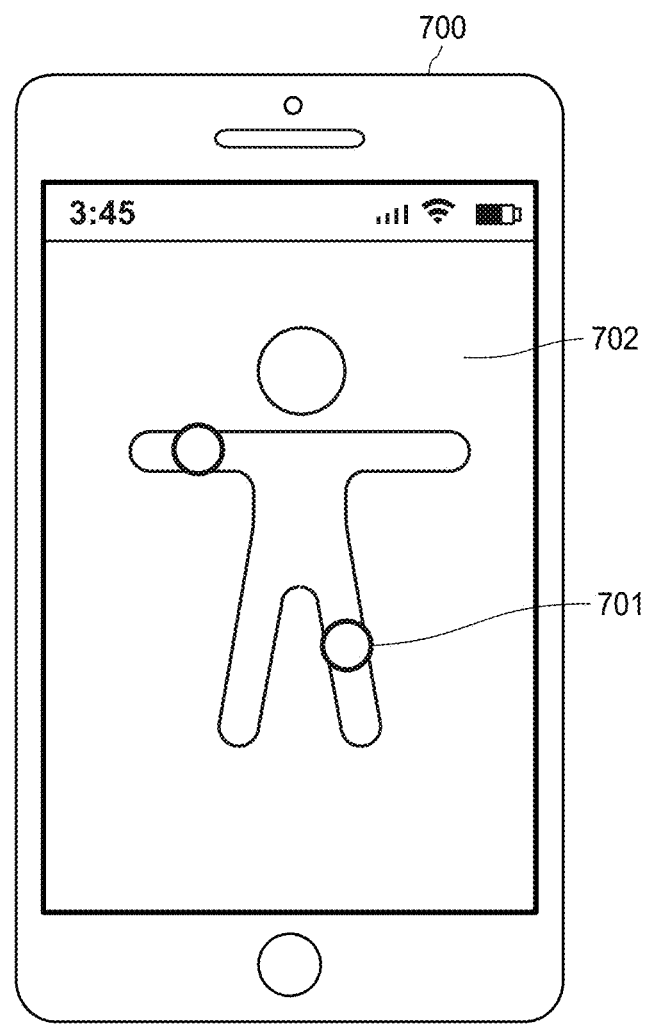
FIG. 7 illustrates a final assessment display which may be presented on the user interface of a client device and which indicates the physical range of motion of different body parts extracted during the coaching phase.

As shown in FIG. 7, the final assessment display 700 includes an outline of a person 702 with indicators 701 overlaid on different body parts/joints which highlight the range of motion for each particular body part/joint. The indicators 701 may be numerical indicators or may be specific shapes, such as circle. The color or size of the shape 701 may indicate the range of motion of the corresponding body/part joint where the shape 701 is located on the person 702. For instance, when a user has a problem moving their right knee and the range of motion category assigned to their right knee is "Very Poor," or "Poor," the final assessment display 700 overlays a red circle 701 on the right knee of the person 702. In another example, when the range of motion category assigned to the user's left elbow is "Good," "Very Good," or "Excellent," the final assessment display 700 overlays a green circle on the left elbow of the person 702.

The final assessment display 700 may also include an indication of the overall range of motion for the user, which may be a numerical indication, a category, or a symbol such as a shape having a particular color. Additionally, the final assessment display 700 may include an indication of the fall risk assessment for the user, which may be a numerical indication, a category, or a symbol such as a shape having a particular color.

Figure 4:
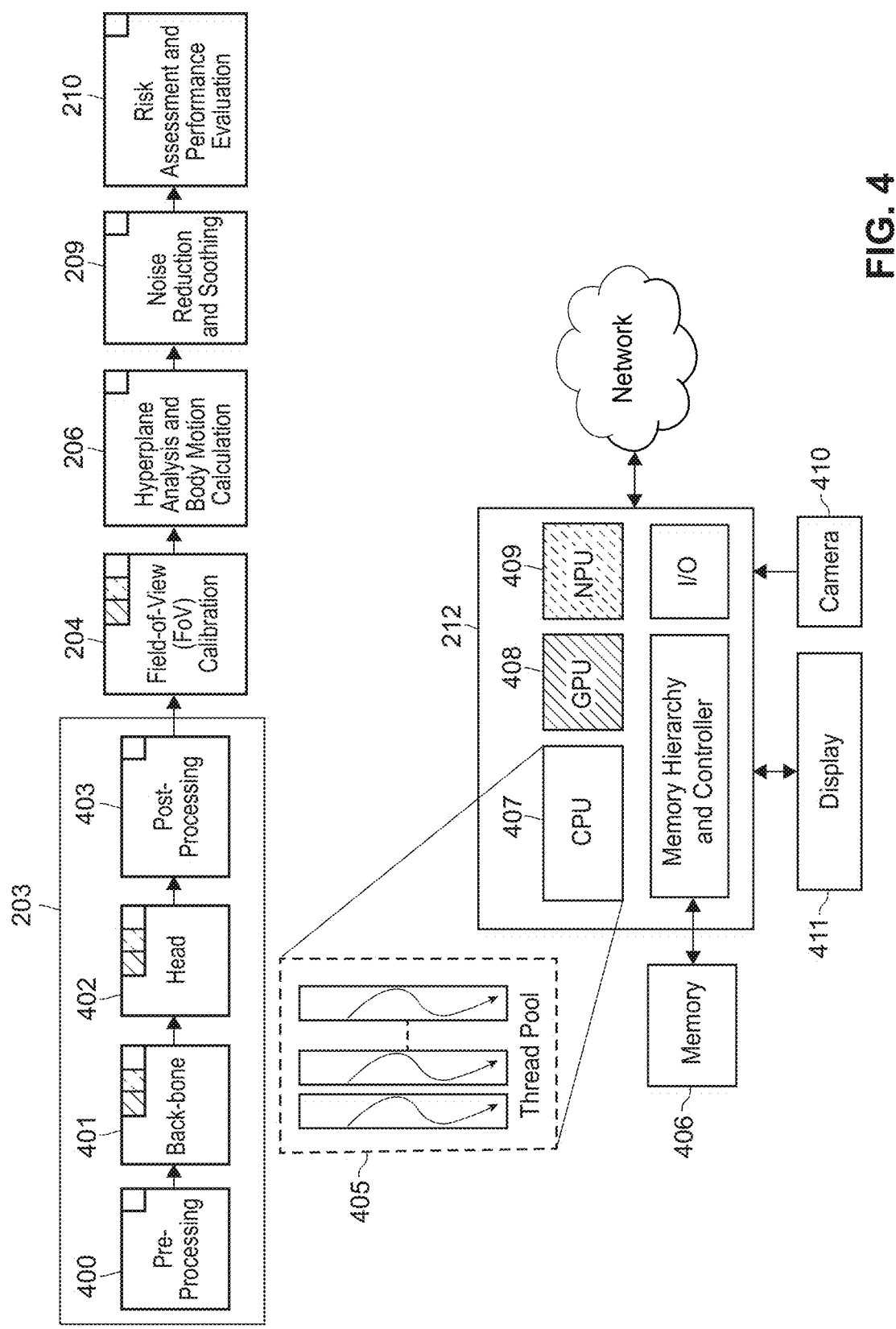
FIG. 4 is a block diagram illustrating how the software components of FIG. 2 can be executed on the hardware components of a computing device.

To generate the 3D skeleton model 205 at block 203, the mobility assessment application include four software components as shown in FIG. 4: a) a pre-processing component 400, b) a backbone component 401, c) a head component 402, and d) a post-processing component 403. The backbone and the head components are trainable and can be fine-tuned based on different applications. The pre-processing and post-processing components should be re-configured based on the input/output size of the backbone and head components.

In addition to determining range of motion metrics for the user and generating performance and fall risk assessments, the mobility assessment application can determine the range of motion of the user in real-time as the user is performing the exercises. Then the mobility assessment application can provide real-time feedback to the user. In some implementations, the real-time feedback may include a display of the 3D skeleton model 205 of the user overlaid on or adjacent to the exercise video so the user has side-by-side comparison of themselves performing the exercise and the person demonstrating the exercise to see if they are performing it correctly.

Figure 6A:
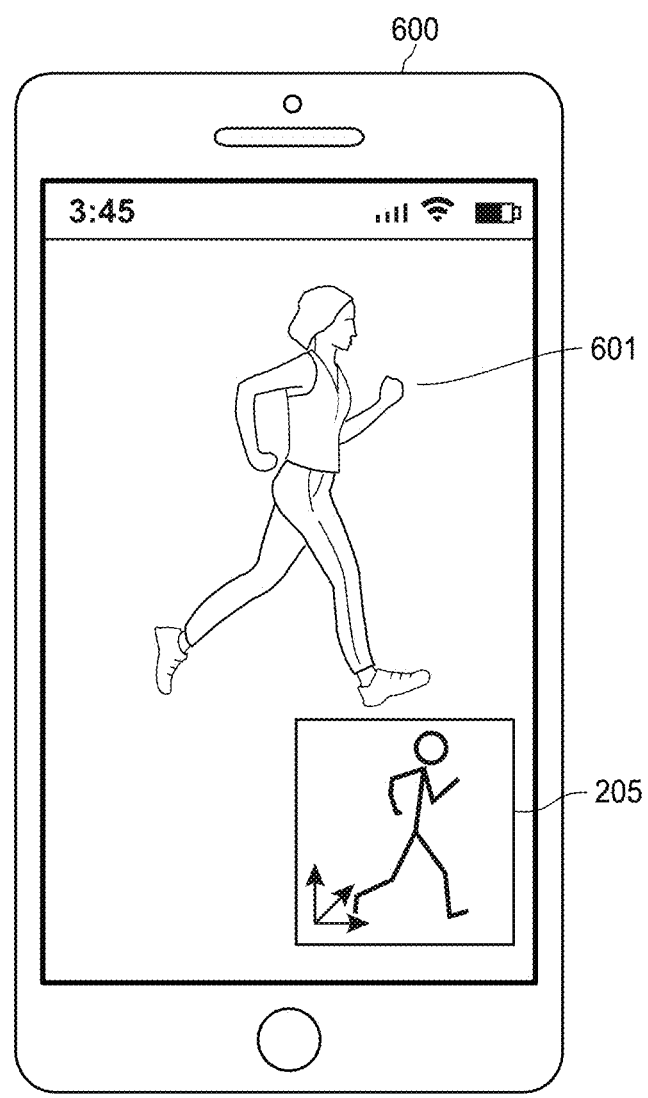
FIGS. 6A and 6B illustrate example exercise coaching displays which may be presented on the user interface of a client device and which present an exercise video demonstrating the exercise along with a 3D skeleton model of the user performing the exercise.
Figure 6B:
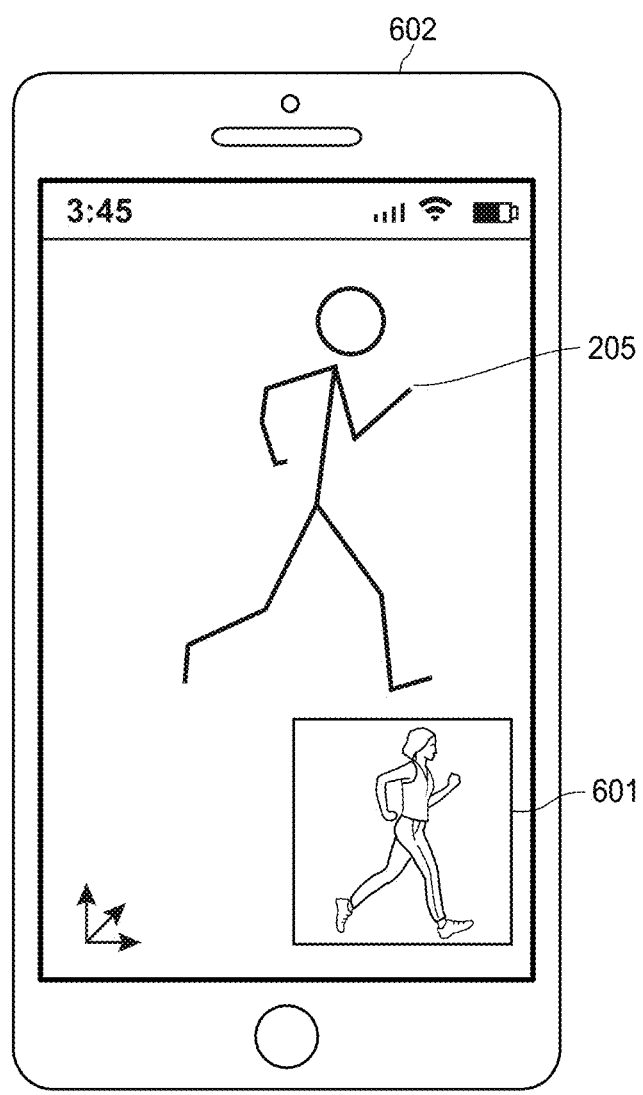

Example exercise coaching displays 600, 602 are illustrated in FIGS. 6A and 6B which may be presented on the user interface 111 of the client computing device 101-104. The example coaching displays 600, 602 present the exercise video 601 demonstrating the exercise in the same display 600, 602 with the 3D skeleton model 205 of the user performing the exercise, so that the user or a PT, fitness trainer, or coach can see how the user is performing the exercise relative to the exercise demonstrated in the video 601.

In some implementations, the exercise video 601 may include tailored exercises and suggestions to enhance user mobility and reduce the risk of falls, focusing on factors such as center of weight, as well as lateral and anterior sways, among others. For example, the mobility assessment application may select a series of exercises tailored to enhance user mobility and reduce the risk of falls based on the user's center of weight and lateral and anterior stays. More specifically, if the user is weak in a particular body part, the mobility assessment application may select exercises from a list of exercises which strengthen that particular body part. In another example, if a particular body part has a limited range of motion, the mobility assessment application may select exercises from the list of exercises which improve range of motion for that particular body part. Then the mobility assessment application may obtain and present an exercise video(s) 601 that includes the selected series of exercises. In other implementations, a PT, fitness trainer, or coach selects the exercises.

While the pre-recorded video of the exercise 601 is displayed, a real-time 3D skeleton model 205 of the user is estimated and shown. Revealing the inferred body skeleton helps the user to see their movements, and based on their evaluated activity, they can improve their performance. The mobility assessment application can also indicate on the display 600, 602 which parts of the body are not performing well and can inform the user by marking the body part on the display, playing an appropriate sound, or providing audio instructions to the user. This approach combines real-time feedback with advanced imaging and modeling technologies to enhance the exercise experience.

Analyzing the movement of the person detected in the images or video to determine the person's range of motion and whether they are performing an exercise properly involves comparing the detected movements against a predefined model of the exercise. This comparison can be done using various metrics, such as the angles between limbs, the speed of movement, and the sequence of movements. Machine learning algorithms can be trained to recognize the correct form of an exercise and identify deviations from this form.

Two display modes are designed for real-time coaching. The first mode 600 as depicted in FIG. 6A is designed for the user. The display 600 shows the exercise video 601 in the larger area and the 3D skeleton model 205 in the smaller area, so that the user can focus on the exercise video 601 since the user is the one who is viewing the display.

The second mode 602 as depicted in FIG. 6B is designed for a PT, fitness trainer, or coach who is executing the mobility assessment application on their client computing device 101-104. In some implementations, the client computing device 101-104 of the PT, fitness trainer, or coach may capture video of the user via a camera at the PT, fitness trainer, or coach's client computing device 101-104. In other implementations, the user's client computing device 101-104 captures the video via a camera and transmits the video frames and/or 3D skeleton models 205 to the PT, fitness trainer, or coach's client computing device 101-104. In any event, the display 602 includes the 3D skeleton model 205 in the larger are and the exercise video 601 in the smaller area to better assist the user. In the displays 600, 602, both the exercise video 601 and the 3D skeleton model 205 are resizable via user controls for the user, PT, fitness trainer, or coach to resize based on their particular needs.

In some implementations, the real-time feedback may also include an indication on the 3D skeleton model 205 highlighting where the user should be moving a particular body part relative to where the user is moving the particular body part. More specifically, the mobility assessment application may annotate the display 600, 602 with an indication of a difference between the movement by the user and the expected motion for the exercise. For example, the mobility assessment application may present a dashed line on the 3D skeleton model 205 next to the line segment representing the user's right arm to show the user where they should be moving their right arm relative to where they currently are moving their right arm. More specifically, when the exercise requires the user to move their right arm in the upward direction at a 90 degree angle relative to their clavicle and the user is only moving their right arm to a 70 degree angle relative to their clavicle, the display may include a dashed line on the 3D skeleton model 205 from the user's clavicle pointing upwards which is perpendicular to the user's clavicle.

Also in some implementations, the real-time feedback may include audio feedback directing the user on how to correct their motion to match the expected motion for the exercise. For example, the mobility assessment application may determine the range of motion for a particular body part/joint of the user and may compare the determined range of motion to an expected range of motion for the exercise. When the determined range of motion differs from the expected range of motion, the mobility assessment application may generate an instruction directing the user on how to correct their motion, and provide the instruction to the user as audio feedback via a speaker. This real-time feedback mechanism is crucial for ensuring that exercises are performed correctly, thereby maximizing the effectiveness of the workout and minimizing the risk of injury.

In some implementations, the mobility assessment application generates the instruction in a natural language format. The mobility assessment application may include an artificial intelligence (AI) trained conversational algorithm (e.g., a natural language processing (NLP) model) that is configured to interact with a user. The NLP model may be or include a machine learning (ML) model (e.g., a large language model (LLM)) trained by the ML module using one or more training data sets of text in order to output one or more training instructions. For example, artificial neural networks, recurrent neural networks, deep learning neural networks, a Bayesian model, and/or any other suitable ML model may be used to train and/or otherwise implement the NLP model. In these aspects, training may be performed by iteratively training the NLP model using labeled training samples (e.g., training user inputs).

The LLM may be a language model for dialogue applications (LaMDA)) included as part of the NLP model. Such an LLM may be conditioned/trained to generate coaching instructions based on characteristics of the instructions, and/or the LLM may be trained to receive a natural language representation of coaching instructions as input and to output a set of text representing the audio response based on the characteristics.

To enable the real-time coaching capability, it is necessary to map the machine learning models and/or other software components to different processing nodes in the client computing device 101-104 to improve efficiency and performance on devices with heterogeneous processing nodes 220, including CPUs 407, Graphical Processing Units (GPUs) 408, and Neural Processing Units (NPUs) 409. FIG. 4 illustrates a block diagram indicating how the software components of FIG. 2 can be executed on the hardware components 405-409 of a client computing device 101-104. The head 402 and backbone 401 of the module for generating the 3D skeleton model 203 and the FOV calibration model 204, which heavily rely on General Matrix Multiplication (GeMM) operations, may be implemented on the CPU 407, GPU 408, and NPU nodes 409. Software blocks with control and casting instructions, including pre-processing 400, post-processing 403, body motion estimation 206, noise reduction 209, and risk assessment 210 may be implemented on the CPU 407. A batching mechanism may be implemented by devices whose CPUs support hyperthreading technology 405 or have multiple cores to speed up the execution time by processing a batch of frames at once.

Figure 8A:
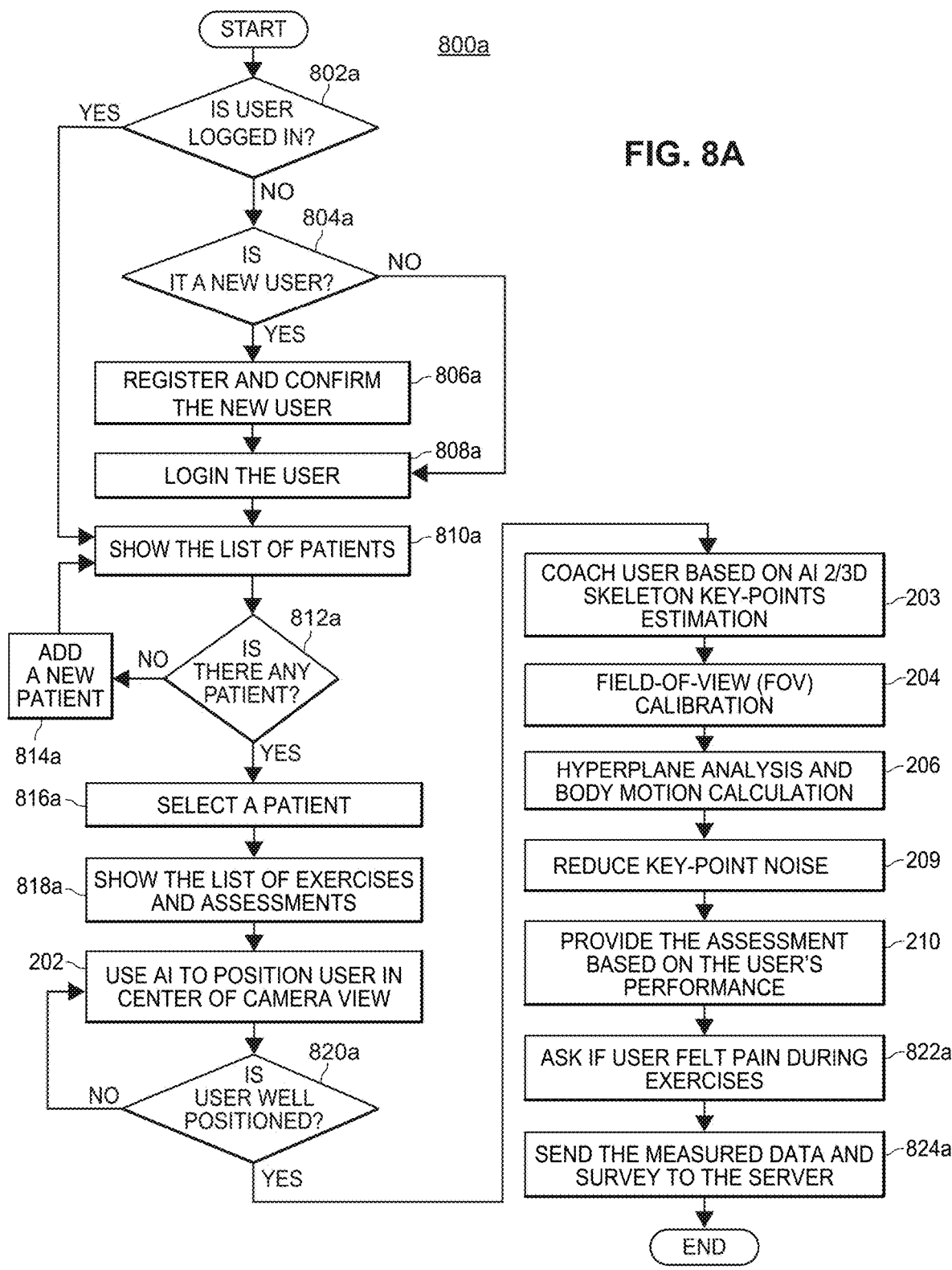
FIG. 8A illustrates a flow diagram of an example method for providing real-time exercise coaching using artificial intelligence, which can be implemented by a client device of a physical therapist, fitness trainer, or coach.
Figure 8B:
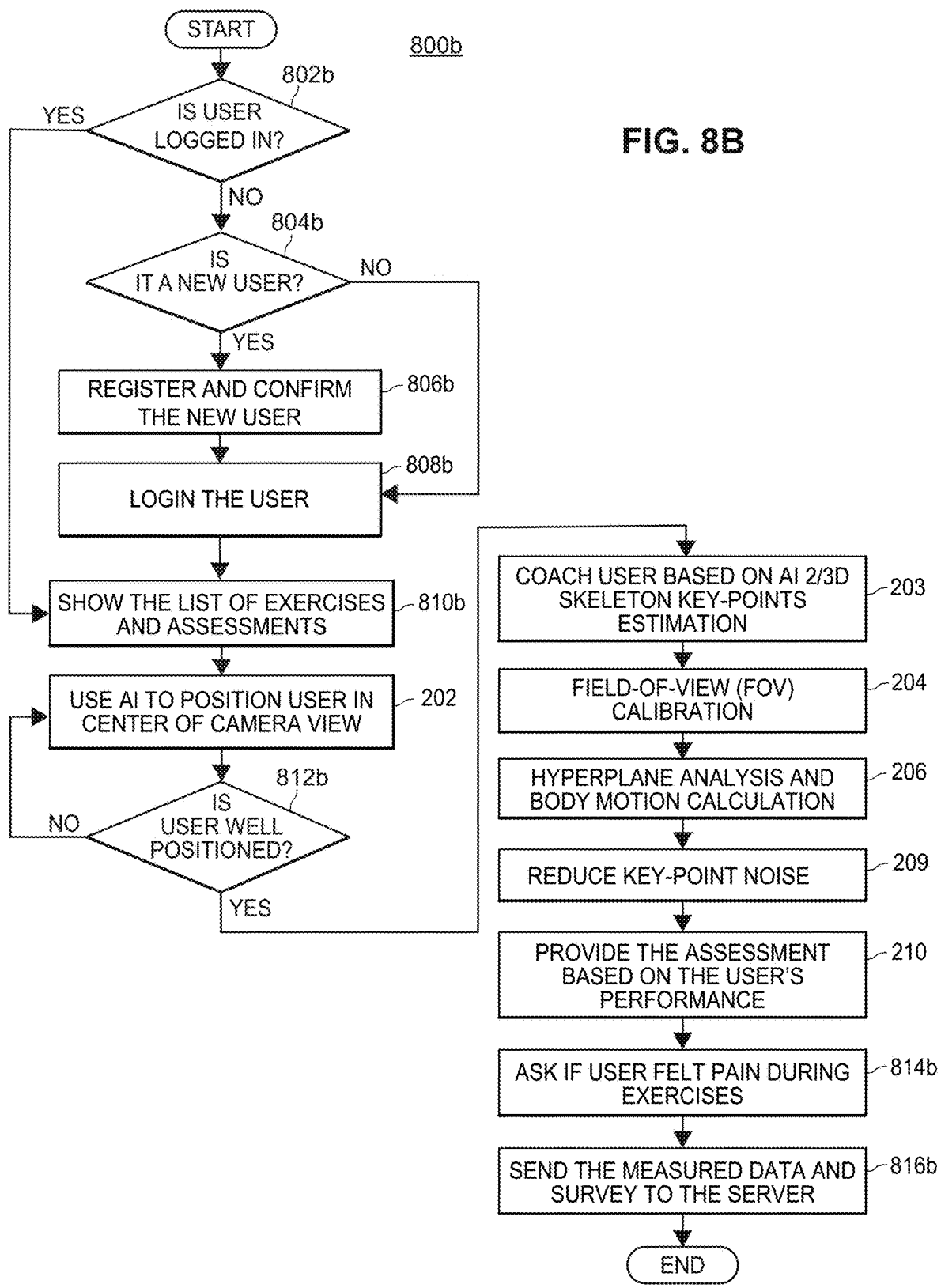
FIG. 8B illustrates a flow diagram of another example method for providing real-time exercise coaching using artificial intelligence, which can be implemented by a client device of a user.

FIGS. 8A and 8B illustrate flow diagrams of example methods 800a, 800b for providing real-time exercise coaching using artificial intelligence. The method 800a can be implemented by a client computing device 101-104 of a PT, fitness trainer, or coach, while the method 800b can be implemented by a client computing device 101-104 of a user.

While the term "user" has been used herein to refer to the person performing the exercises, the term "user" in the method 800a is used to refer to the PT, fitness trainer, or coach who may be monitoring the person performing the exercises, either remotely or in person. In any event, at blocks 802a-808a the user logs into the mobility assessment application. For example, upon launching the mobility assessment application or a website for the mobility assessment, the user may be prompted to enter login credentials which may be provided to the server device 106 and verified as corresponding to a stored user profile. In other implementations, the login credentials may be stored at the client computing device 101-104 and may automatically be sent to the server device 106 upon launching the mobility assessment application or navigating to the mobility assessment website. If the user is a new user, the user may need to register for a user profile with the mobility assessment system (block 806*a*).

In any event, at block 810*a*, the mobility assessment application may present a list of registered patients or people who are performing the exercises which may be associated with the user. For example, the user may previously have indicated that they are assisting in exercise coaching for the patient. If there is no registered patient, the user can add one to their list via user controls provided by the mobility assessment application (block 814*a*).

Then upon selecting a patient (block 816*a*), the mobility assessment application may select a set of exercises for the patient (block 818*a*). For example, if this is an initial assessment for the patient, the mobility assessment application may select all of the exercises for the patient to perform so that the patient's mobility can be assessed completely for each of their body parts/joints. After the initial assessment, the mobility assessment application may identify body parts/joints where the patient's mobility needs the most improvement. Accordingly, the mobility assessment application may select exercises which focus on these body parts/joints in subsequent assessments. For example, in the initial assessment, the mobility assessment application may select ten different exercises which test the mobility of the patient's entire body. However, after the patient has performed several mobility assessments, and the patient's mobility is good everywhere except the patient's ankles, the mobility assessment application may select a subset of the exercises for improving the patient's ankle mobility.

In any event, at blocks 202 and 820*a*, the camera frame and patient's position is calibrated to ensure the patient is in the right spot and the IoU meets the predefined thresholds (block 202 and 809).

During the next step, the AI-based coaching algorithm (block 203) plays exercise videos for the selected exercises while giving feedback on the patient's movement by displaying the 3D skeleton model. In this stage, the user may select either display mode 600 or 602 as shown in FIGS. 6A and 6B based on the user or patient's preference.

After processing the video frames for a specific exercise and performing the FoV calibration (block 204), the mobility assessment application analyzes the patient's range of motion (block 206). Next, the mobility assessment application reduces and smooths noise to remove any sudden movement and errors (block 209). Finally, the patient is assessed by for example, applying the user's preferred weighted function and/or thresholds to the ranges of motion for the patient's body parts/joints extracted from the different exercises (block 210). The user may also request the patient to provide feedback regarding whether the patient felt any paint during the exercises (block 822*a*). At block 824*a*, the mobility assessment application may provide the final assessment and the patient feedback to the server device 106 for storage in the database 105 to track the patient's progress over multiple mobility assessments.

The method 800*b* as shown in FIG. 8B includes similar steps as the method 800*a*. However, in the method 800*b* the user is the person performing the exercise. In the method 800*b*, a PT, fitness trainer, or coach may not be involved at all. Instead, the user may be trained solely via the AI-based coaching of the mobility assessment application.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A method for assessing mobility of a user, the method comprising:
    obtaining, at one or more processors from a camera, a video of a user having a plurality of video frames;
    generating, by the one or more processors, a three-dimensional (3D) skeleton model of the user based on the plurality of video frames;
    determining, by the one or more processors, a range of motion of the user based on a change in position of the 3D skeleton model over the plurality of video frames; and
    providing, by the one or more processors, an indication of the range of motion of the user for display including presenting, by the one or more processors, a display of the 3D skeleton model with real-time changes in position as the user changes position to provide real-time feedback of the range of motion of the user.

2. The method of claim 1, wherein the 3D skeleton model includes a plurality of 3D vectors representing a plurality of body parts of the user.

3. The method of claim 2, wherein determining the range of motion of the user includes:
    for a particular joint, determining, by the one or more processors, a range of motion of the joint connecting a first body part to a second body part based on an angle of the first body part with respect to the second body part.

4. The method of claim 3, further comprising:
    determining, by the one or more processors, the range of motion of the user based on ranges of motion of each of a plurality of joints.

5. The method of claim 3, wherein providing the indication of the range of motion of the user includes:
    providing, by the one or more processors, indications of the ranges of motion of each of the plurality of joints for display.

6. The method of claim 3, further comprising:
determining, by the one or more processors, the angle of the first body part with respect to the second body part by generating a hyperplane perpendicular to the first body part and determining an angle of a 3D vector representing the second body part with respect to the hyperplane.

7. The method of claim 1, further comprising:
calibrating, by the one or more processors, the user to stand in a center of a camera view of the camera by:
determining, at the one or more processors, a position of the user with respect to the camera view; and
providing, by the one or more processors, instructions for the user to move to the center of the camera view based on the position of the user relative to the center of the camera view.

8. The method of claim 1, further comprising:
obtaining, by the one or more processors, a field of view calibration model trained using known user motion data at a plurality of camera angles; and
applying, by the one or more processors, 3D vector data from the plurality of video frames to the field of view calibration model to adjust the 3D skeleton model for the plurality of video frames in accordance with a camera angle of the camera relative to the user.

9. The method of claim 1, further comprising:
performing, by the one or more processors, a fall risk assessment based on the range of motion of the user to determine a risk of falling for the user.

10. The method of claim 9, further comprising:
providing, by the one or more processors, an indication of the fall risk assessment for display to the user.

11. The method of claim 9, further comprising:
selecting, by the one or more processors, one or more exercises tailored to the user to enhance user mobility and reduce the risk of falling for the user; and
presenting, by the one or more processors, an exercise video to the user including the one or more exercises.

12. The method of claim 1, wherein providing an indication of the range of motion of the user for display includes presenting an indicator overlaid on a representation of a body part for the user which highlights the range of motion for the user's body part.

13. A computing device for assessing mobility of a user, the computing device comprising:
a user interface;
one or more processors; and
a non-transitory computer-readable memory storing instructions thereon, that when executed by the one or more processors, cause the computing device to:
obtain, from a camera, a video of a user having a plurality of video frames;
generate a three-dimensional (3D) skeleton model of the user based on the plurality of video frames;
determine a range of motion of the user based on a change in position of the 3D skeleton model over the plurality of video frames; and
provide, via the user interface, an indication of the range of motion of the user for display including present a display of the 3D skeleton model with real-time changes in position as the user changes position to provide real-time feedback of the range of motion of the user.

14. The computing device of claim 13, wherein the 3D skeleton model includes a plurality of 3D vectors representing a plurality of body parts of the user.

15. The computing device of claim 14, wherein to determine the range of motion of the user, the instructions cause the computing device to:
for a particular joint, determine a range of motion of the joint connecting a first body part to a second body part based on an angle of the first body part with respect to the second body part.

16. The computing device of claim 15, wherein the instructions further cause the computing device to:
determine the angle of the first body part with respect to the second body part by generating a hyperplane perpendicular to the first body part and determining an angle of a 3D vector representing the second body part with respect to the hyperplane.

17. The computing device of claim 13, wherein the instructions further cause the computing device to:
calibrate the user to stand in a center of a camera view of the camera by:
determining a position of the user with respect to the camera view; and
providing instructions for the user to move to the center of the camera view based on the position of the user relative to the center of the camera view.

18. The computing device of claim 13, wherein the instructions further cause the computing device to:
obtain a field of view calibration model trained using known user motion data at a plurality of camera angles; and
apply 3D vector data from the plurality of video frames to the field of view calibration model to adjust the 3D skeleton model for the plurality of video frames in accordance with a camera angle of the camera relative to the user.

19. The computing device of claim 13, wherein the instructions further cause the computing device to:
perform a fall risk assessment based on the range of motion of the user to determine a risk of falling for the user.

* * * * *